(12) United States Patent
Yablon

(10) Patent No.: US 8,860,934 B2
(45) Date of Patent: Oct. 14, 2014

(54) SYSTEM AND METHOD FOR MEASURING AN OPTICAL FIBER

(75) Inventor: Andrew D. Yablon, Livingston, NJ (US)

(73) Assignee: Interfiber Analysis, LLC, Sharon, MA (US)

(*) Notice: Subject to any disclaimer, the term of this patent is extended or adjusted under 35 U.S.C. 154(b) by 83 days.

(21) Appl. No.: 13/350,626

(22) Filed: Jan. 13, 2012

(65) Prior Publication Data

US 2013/0182243 A1    Jul. 18, 2013

(51) Int. Cl.
*G01N 21/00* (2006.01)
(52) U.S. Cl.
USPC ........................................... 356/73.1
(58) Field of Classification Search
USPC ............ 356/73.1; 359/341.41, 337, 344, 326, 359/341.1; 385/73, 95, 123; 600/436; 73/705; 372/6, 75
See application file for complete search history.

(56) References Cited

U.S. PATENT DOCUMENTS

| | | | | |
|---|---|---|---|---|
| 4,551,020 A * | 11/1985 | Reid et al. | | 356/73.1 |
| 4,847,851 A * | 7/1989 | Dixon | | 372/75 |
| 6,626,043 B1 * | 9/2003 | Bailey et al. | | 73/705 |
| 7,559,706 B2 * | 7/2009 | Tammela et al. | | 385/95 |
| 8,373,852 B2 * | 2/2013 | Ruchet et al. | | 356/73.1 |
| 2002/0018287 A1 * | 2/2002 | Zellmer et al. | | 359/341.1 |
| 2004/0105144 A1 * | 6/2004 | Yang et al. | | 359/341.41 |
| 2007/0297044 A1 * | 12/2007 | Qiao et al. | | 359/337 |
| 2009/0201953 A1 * | 8/2009 | Peyghambarian et al. | | 372/6 |
| 2009/0252468 A1 * | 10/2009 | Sugizaki et al. | | 385/123 |
| 2009/0262337 A1 * | 10/2009 | Nicholson et al. | | 356/73.1 |
| 2009/0296199 A1 * | 12/2009 | Franjic et al. | | 359/344 |
| 2010/0124394 A1 * | 5/2010 | Meek et al. | | 385/73 |
| 2012/0134011 A1 * | 5/2012 | Fujiwara et al. | | 359/326 |
| 2012/0232385 A1 * | 9/2012 | Hattori et al. | | 600/436 |

OTHER PUBLICATIONS

C. Degen, I. Fischer and W. Elsäßer, "Transverse modes in oxide confined VCSELs: Influence of pump profile, spatial hole burning, and thermal effects," Aug. 2, 1999 / vol. 5, No. 3 / Optics Express 38.*
Tajamal Bhutta et al, "Spatial dopant profiles for transverse-mode selection in multimode waveguide", Jul. 2002, vol. 19, No. 7/Optical Society of America.*
Kirchhof, et al, "Spatial Distribution Effects and Laser Efficiency in Er/Yb Doped Fibers," SPIE, vol. 5350, Bellingham, WA, 2004. pp. 222-233.
Unger, et al, "Codoped Materials for High Power Fiber Lasers—Diffusion Behaviour and Optical Properties," SPIE, vol. 6469, Downloaded Dec. 17, 2010, pp. 646913-1-646913-12.
Yablon, "Measuring the Spatial Distribution of Rare-Earth Dopants in High-Power Optical Fibers," SPIE, vol. 7914, 2011, pp. 7914IN-1-7914IN-8.
Yablon, "New Transverse Techniques for Characterizing High-Power Optical Fibers," Optical Engineering, vol. 50(11), Nov. 2011, pp. 111603-1-111603-6.

* cited by examiner

*Primary Examiner* — Tarifur Chowdhury
*Assistant Examiner* — Jamil Ahmed
(74) *Attorney, Agent, or Firm* — Berkeley Law & Technology Group, LLP

(57) ABSTRACT

Subject matter disclosed herein relates to measuring optical fibers, and, in particular, to measuring spontaneous emission produced in an optical fiber.

22 Claims, 3 Drawing Sheets

Gain-producing core region of optical fiber

SYSTEM AND METHOD FOR MEASURING AN OPTICAL FIBER

BACKGROUND

1. Field

Subject matter disclosed herein relates to measuring optical fibers, and, in particular, to measuring spontaneous emission produced in an optical fiber.

2. Information

An optical fiber may comprise a flexible, transparent fiber made of any of a number of materials, such as glass or plastic. An optical fiber may function as a waveguide, or "light pipe", to transmit light between the two ends of the fiber, for example. An optical fiber may include a transparent core surrounded by a transparent cladding material with a lower index of refraction. Light may be kept in an optical fiber by total internal reflection or by a process involving a photonic bandgap of a photonic crystal optical fiber, thus providing a mechanism for the optical fiber to act as a waveguide. Optical fibers that support multiple propagation paths or transverse modes are called multi-mode fibers (MMF), while those that support a single mode are called single-mode fibers (SMF).

Optical fibers may be used as optical sources or optical amplifiers, in which case gain-producing dopants, such as rare-earth ions, for example, may be incorporated into the structure of the optical fibers. Performance of such optical sources or optical amplifiers may depend, at least in part, upon spatial distribution of gain-producing dopants or gain efficiency of the dopants.

BRIEF DESCRIPTION OF THE DRAWINGS

Non-limiting and non-exhaustive embodiments will be described with reference to the following figures, wherein like reference numerals refer to like parts throughout the various figures unless otherwise specified.

DETAILED DESCRIPTION

Figure 1:
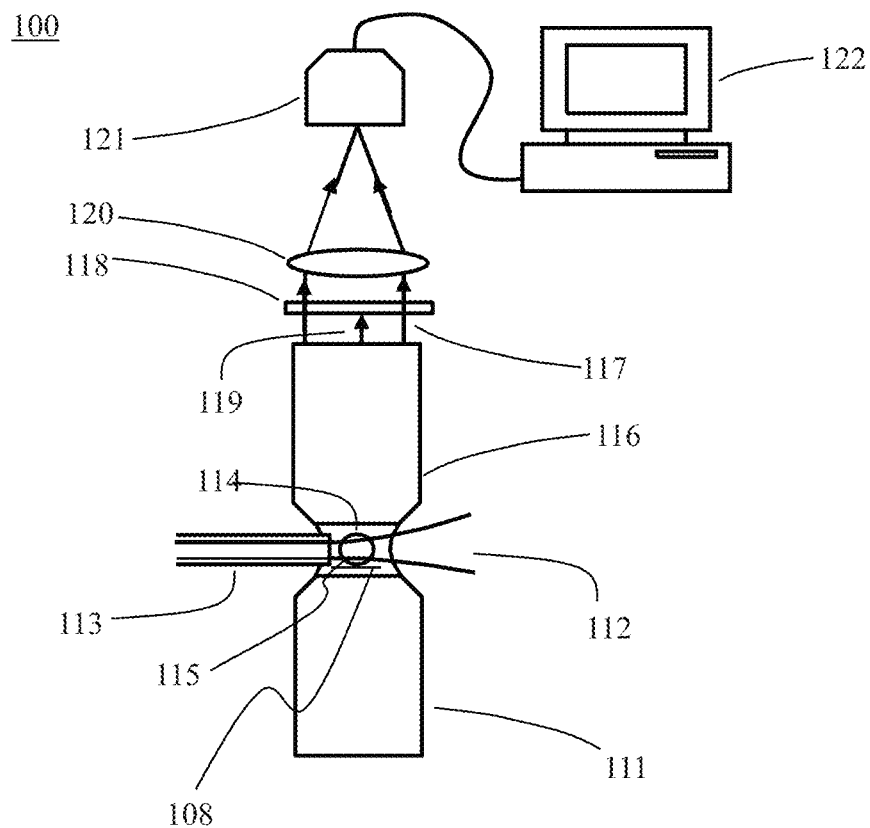
FIG. 1 is a schematic diagram of a spontaneous emission measurement system, according to an embodiment.

Reference throughout this specification to "one embodiment" or "an embodiment" means that a particular feature, structure, or characteristic described in connection with an embodiment is included in at least one embodiment of claimed subject matter. Thus, appearances of the phrase "in one embodiment" or "an embodiment" in various places throughout this specification are not necessarily all referring to the same embodiment. Furthermore, particular features, structures, or characteristics may be combined in one or more embodiments.

Optical fibers may comprise a host material (e.g., fused silica glass) with one or more chemical dopant species, such as germanium oxide, for example. In this context, "optical fiber", which may comprise a light guide, means a medium capable of transmitting an electromagnetic signal using total internal reflection or by a photonic bandgap process. For example, an optical fiber may comprise a relatively slender cylinder or fiber made of any of a number of materials, such as glass or plastic. An optical fiber may have a cross-sectional shape comprising any of a number of shapes, such as circular, oval, rectangular, just to name a few examples.

Chemical dopant species may modify host properties, such as, for example, a refractive index of the host. If one or more chemical dopant species modify a local refractive index of an optical fiber, as in the case of germanium oxide doped fused silica, for example, the optical fiber may be called a "passive" optical fiber. A passive optical fiber may transport or modify an optical signal, but may lack an ability to amplify the signal's optical power. In this context, "optical signal" means one or more electromagnetic waves having time or position dependent amplitudes. However, certain chemical species, for example rare-earth elements such as Ytterbium, may produce optical gain (e.g., amplification) if doped into a host material. An optical fiber containing power amplification capabilities may be called an "active" optical fiber. In this case, an optical pump signal, such as, for example, 976 nanometer (nm) light, may be injected into an active fiber to excite gain-producing dopant species so that an optical signal at a different optical wavelength, such as, for example, 1060 nm light, may be amplified to a higher power level. The term "optical pump signal" means an optical signal used to induce spontaneous emission by atoms or molecules by impinging on the atoms or molecules. In this context, "spontaneous emission" means a process by which a light source such as an atom or molecule in an excited state undergoes a transition to a state with a lower energy (e.g., a ground state) and emits one or more photons. An optical pump signal may be introduced from either end of an active optical fiber, or from a side of the active optical fiber. However, an optical pump signal may be arranged to propagate axially along the length of active optical fiber since axial propagation may provide a relatively long interaction length between pump signal wavelength, gain-producing dopant species, and the optical signal to be amplified.

A precise spatial distribution of gain in an active optical fiber may be a factor affecting performance, such as amplification efficiency, for example, of the active optical fiber. Furthermore, active optical fiber designs may employ on relatively complex spatially inhomogeneous distributions of gain-producing dopants for proper operation. Some embodiments may provide techniques for determining spatial distribution of gain in an active optical fiber, which may be difficult to determine using other techniques. In one embodiment, spontaneous emission produced by a homogeneously pumped active optical fiber may be measured in a spatially resolved manner, and because of the homogeneous pumping, this spontaneous emission may be considered to be spatially resolved optical gain in the active optical fiber. In this context, "spatially resolved spontaneous emission" means a measurement of spontaneous emission substantially or at least approximately as a function of position, such as a position of an optical fiber, for example. While embodiments may not be able to distinguish among spatial variations in a host glass and spatial variations in one or more dopant species, in many cases a measured signal may be assumed to be a local concentration of dopant species. Advantageously, embodiments need not involve axial pumping of an active optical fiber, and therefore need not involve convolving a measured spontaneous emission signal with pump signal spatial inhomogeneities resulting from axial fiber modes. For example, axial optical pumping may lead to single-mode or multi-mode optical signal transmission that may significantly impact measuring spatial distribution of spontaneous emission. On the other hand, transverse optical pumping may be performed in a manner so as to not lead to single-mode or multi-mode optical signal transmission at a wavelength of the transverse pump irradiation sufficient to significantly impact measuring spatial distribution of spontaneous emission.

In an embodiment, type, spatial distribution, or optical gain efficiency of gain-producing dopants in an optical fiber may be determined, at least in part, by measuring a spatial distribution of spontaneous emission of the dopants while the fiber and dopants are exposed to optical pumping. In an implementation, a technique for determining a type (e.g., chemical specie) of one or more dopants or for measuring spatial distribution or optical gain efficiency of one or more dopants in an optical fiber may include exposing an optical fiber to a transverse pump signal to transversely irradiate the optical fiber and measure spatial distribution of spontaneous emission produced in the optical fiber in response to the transverse pump signal. A transverse pump signal may comprise substantially homogeneous transverse pump irradiation, though claimed subject matter is not so limited. For example, transverse pump irradiation incident on a portion of an optical fiber may be substantially uniform in amplitude or wavelength over the portion of the optical fiber.

In a particular embodiment, spatial distribution of spontaneous emission of an optical fiber may be measured at multiple angles of rotation. Spatial distribution of spontaneous emission measured at a multiplicity of angles may be processed into a two dimensional cross-sectional representation of the spontaneous emission, such as by using computerized tomography. Tomography may involve collecting signal samples, for example, of spontaneous emission in multiple directions and providing the signal samples to any of a number of tomographic reconstruction software processes processed by a computer processor.

In an embodiment, a system for measuring spatial distribution of spontaneous emission produced in an optical fiber may include an optical pumping source to produce an electromagnetic signal (e.g., electromagnetic radiation) and a delivery system to deliver the signal. A system may also include a lens system and a detector used to generate an image, and a computer to process the image, for example. Some embodiments may provide cost or convenience benefits in that a measurement system embodiment may be readily assembled from commercially available components, for example.

In a particular embodiment, a system for measuring spatial distribution of spontaneous emission produced in an optical fiber may include a pump signal source to transversely irradiate the optical fiber with an optical pump signal to produce the spontaneous emission. A pump signal incident on a portion of an optical fiber may be substantially uniform in amplitude or wavelength over the portion of the optical fiber, though claimed subject matter is not so limited. One or more optical components, such as an objective lens for example, may be used to produce an image of spontaneous emission. In a particular implementation, a multi-pixel detector may be used to convert an optical image to digital electronic signals representative of a measured spatial distribution of spontaneous emission. Measured spatial distribution of spontaneous emission of an optical fiber may comprise measured spontaneous emission amplitude as a function of spatial position about the optical fiber.

FIG. 1 is a schematic diagram of a spontaneous emission measurement system embodiment, such as 100, according to an embodiment. An optical fiber 114 may be positioned between a lower condenser lens 111 and an upper imaging lens 116, either of which may comprise oil immersion objective lenses, for example. A refractive index fluid or gel 115, such as an index matching fluid, for example, may be placed in a region surrounding optical fiber 114. An index fluid may comprise a liquid or gel having a refractive index relatively close or similar to a refractive index of an optical element (e.g., an optical fiber) with which the index fluid makes contact. Index fluid 115 may be held by surface tension between lenses 111 and 116, for example. This fluid may be selected to be relatively close to a refractive index (e.g., approximately 1.45 for silica optical fibers) of cladding of optical fiber 114. In FIG. 1, optical fiber 114 is shown in cross-section. In one implementation, optical fiber 114 may be mounted to a rotation stage 108 that allows the optical fiber to be rotated about its axis to any of a variety of rotation angles relative to upper imaging lens 116. In another implementation, rotation stage 108 may comprise a multi-axis translation stage on which optical fiber 114 may be mounted. A rotation stage or a multi-axis translation stage may allow precisely controlled displacements relative to system 100, for example.

Pump signal beam 112, which may comprise a diffracting electromagnetic field, may be introduced to optical fiber 114, for example, by a step-index single-mode or multimode pump fiber 113. Pump signal beam 112 may be transversely incident on optical fiber 114. For example, an axis of pump fiber 113 may be substantially perpendicular to an axis of optical fiber 114, though claimed subject matter is not limited in this respect. In one implementation, optical fiber 114 may be positioned in a near-field region of pump signal beam 112 so that optical fiber 114 is subjected to a substantially homogeneous pump signal. Pump fiber 113 may be cleaved or polished to produce a high optical-quality end face and may be inserted into refractive index fluid 115. Inserting an end face of pump fiber 113 into refractive index fluid 115 may reduce refraction or diffraction of a pump signal exiting the end face, which may lead to substantially homogeneous pump radiation reaching optical fiber 114, for example. In other words, refractive index fluid 115 may be used to optically connect pump fiber 113 to optical fiber 114 to reduce attenuation or scattering losses of a pump signal. Pump fiber 113 may also be terminated with a lens, for example, such as a section of graded-index multimode fiber that may produce a substantially collimated beam of pump signal beam 112, though claimed subject matter is not so limited. A substantially homogeneous distribution of a pump signal may facilitate that any variations in spontaneous emission detected by an array detector 121 (described in further detail below) correspond to variations in optical fiber 114 being measured. Pump signal beam 112 may be sufficiently dispersed to cover a portion of the optical fiber 114. Position of the pump signal beam 112 (e.g., position of pump beam end face) may be adjusted relative to optical fiber 114 to help facilitate desirable alignment between beam 112 and optical fiber 114.

Optically pumping optical fiber 114 transversely across an optical fiber rather than axially may offer several benefits. For example, transverse path length across optical fiber 114 may be on the order of 100 microns, which may be a short enough distance that a pump signal beam may be maintained relatively collimated across the optical fiber. A relatively collimated beam may help facilitate that local pump signal amplitude is substantially constant across optical fiber 114. Furthermore, a pump signal may be treated as homogeneous because depletion of a pump signal by absorption by dopant species present in optical fiber 114 as the pump signal traverses optical fiber 114 may be relatively small or negligible over a relatively short distance (e.g., 100 microns). As another benefit of transversely optically pumping an optical fiber, effects of refractive index variations in optical fiber 114 may be reduced and a modal structure of optical fiber 114 may not significantly affect spontaneous emission measurements.

In another implementation, a pump signal need not be conveyed from a light source via a cleaved fiber. Instead, a pump signal may be produced using free-space optics. For example, an optical system that produces a substantially homogeneous distribution of a pump signal across an optical fiber may comprise a suitable technique for optical pumping. Of course, details of system 100 are merely examples, and claimed subject matter is not so limited.

A pump signal may be selected based, at least in part, on wavelength. For example, a desirable pump signal may comprise a wavelength or range of wavelengths that excite gain-producing dopants in an optical fiber so as to produce spontaneous emission upon or after dopant relaxation. A pump signal need not comprise visible wavelengths, but may also comprise infrared and/or ultraviolet (UV) wavelengths. For example, a dopant Yb may be associated with a pumping wavelength approximately 975 ran, which may be used to more efficiently produce spontaneous emission from about 1000 nm to about 1100 nm. Accordingly, a commercially available 976 nm fiber-coupled pump diode laser having a power of approximately 100 milliwatts (mW) may be desirable for use with Yb dopant, just to give an example of a suitable light source.

Returning to FIG. 1, lens 116 may be used to form an image of spontaneous emission produced in optical fiber 114 in response to transversely incident pump signal beam 112. In one particular implementation, a lens 120, such as a tube lens, for example, may be used with lens 116 to project, an image of spontaneous emission onto array detector 121. In another particular implementation, lens 116 may comprise an oil-immersion objective that may achieve a relatively high numerical aperture image to allow for a relatively fine resolution image. Array detector 121 may comprise a two-dimensional array or a linear array detector, such as an array of pixilated charge-coupled devices (CCD) or one or more complementary metal-oxide-semiconductor (CMOS) devices, just to name a couple of examples. Elements (e.g., pixels) of a linear array detector may be aligned so that individual elements correspond to a particular radial position in an image of spontaneous emission of an optical fiber under test (e.g., optical fiber 114).

In one embodiment, propagation direction of pump signal beam 112 may be such that a diffracting beam of pump signal beam 112 is not captured by lens 116. An arrangement may reduce an effect of spurious pump radiation from pump signal beam 112 being detected by array detector 121, for example. Furthermore, an optical filter 118 may be used to substantially attenuate scattered pump radiation 119 propagating in a direction toward array detector 121. Optical filter 118 may selectively filter scattered pump radiation 119 while permitting spontaneous emission 117 to reach array detector 121 relatively un-attenuated.

Array detector 121 may provide an electronic signal representative of an image to computer 122. Computer 122 may comprise a processor to execute an application that determines spatial distribution of spontaneous emission inside optical fiber 114 based, at least in part, on an image provided by detector 121, for example. If optical fiber 114 is substantially axisymmetric, an inverse Abel integral may be used to relate transverse amplitude (e.g., of an image) provided by array detector 121 to a spontaneous emission profile in optical fiber 114. On the other hand, if optical fiber 114 is not substantially axisymmetric, computerized tomography may be used to compute non-axisymmetric spontaneous emission profile using transverse amplitude (e.g., image) provided by array detector 121 at a multiplicity of rotational angles, for example. An inverse Radon transform comprises one of a number of types of tomographic processes that may be used, though claimed subject matter is not limited in this respect.

In one embodiment, lower condenser lens 111 may be used to introduce illumination light for microscopic examination of position or structure of optical fiber 114. For example, optical fiber 114 may be located and brought to focus using microscopy techniques and subsequently interrogated (e.g., measured) using a pump signal. In another embodiment, lower condenser lens 111 may be replaced by a substrate or other structure to retain refractive index fluid 115 in a region about optical fiber 114, for example.

In another embodiment, system 100 may be operated at any of a number of various wavelengths of a pump signal so that correspondingly different spatial distributions of spontaneous emission may be incited or detected. One dopant species may produce spontaneous emission if pumped at a wavelength at which another species is substantially inactive, for example. Accordingly, spontaneous emission contributions associated with distinct dopant species may be differentiated from one another.

Figure 2A:
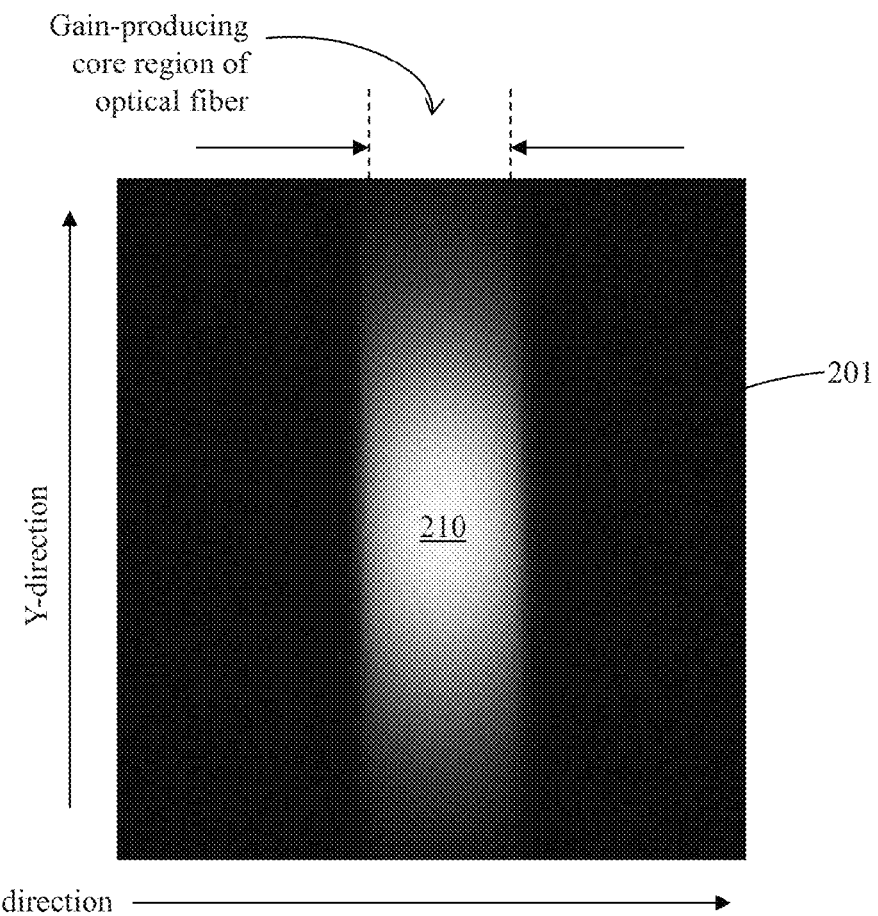
FIG. 2A is an image of spontaneous emission, according to an embodiment.
Figure 2B:
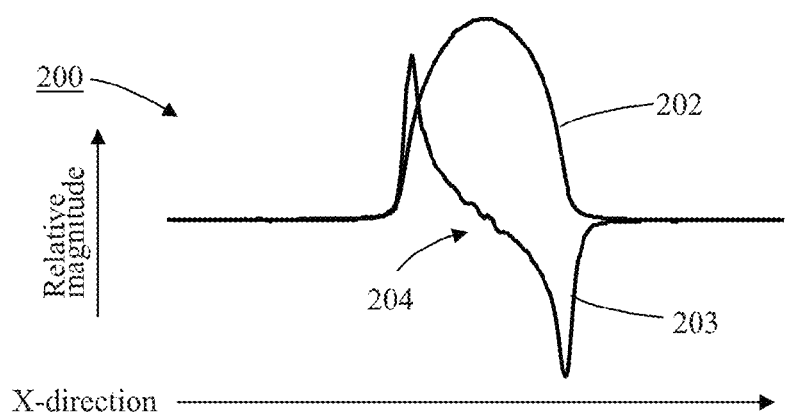
FIG. 2B includes a distribution graph of spontaneous emission, according to an embodiment.

FIGS. 2A and 2B include an image 201 of spontaneous emission of an optical fiber and a distribution graph 200 of the spontaneous emission, according to an embodiment. X-direction of image 201 may comprise a transverse direction, substantially perpendicular to an axis of the optical fiber. Y-direction of image 201 may comprise an axial direction, substantially parallel to an axis of the optical fiber. Spontaneous emission induced by a pump signal incident in an X-direction may lead to a bright region 210, wherein brightness in image 201 may correspond to spontaneous emission amplitude, for example. Distribution or placement of gain-producing dopants in an optical fiber may lead to a particular distribution of spontaneous emission amplitude (e.g., distribution of brightness in image 201). Accordingly, a technique for measuring a distribution or placement of gain-producing dopants in an optical fiber may include evaluating a plot of spontaneous emission amplitude as a function of position with respect to an optical fiber. For example, plot 202 comprises a transverse amplitude profile of spontaneous emission 210. X-direction in FIG. 2B may correspond to X-direction in FIG. 2A. A vertical direction for plots 202 and 203 may correspond to relative amplitudes, respectively. Plot 203 comprises a first derivative of plot 202, which may visually show fine structure of plot 202. For example, plot 203 may show ripples 204 associated with fine structure inside a core of an optical fiber being measured.

For example, a commercially available, active optical fiber may be transversely optically pumped to produce image 201 of spontaneous emission. In a particular example, spontaneous emission image 201 may be produced by measuring a 25.0 micron diameter Yb-doped core optical fiber detected by a silicon CCD array detector, such as array detector 121, though claimed subject matter is not limited to any particular details of any illustrative examples.

Figure 3:
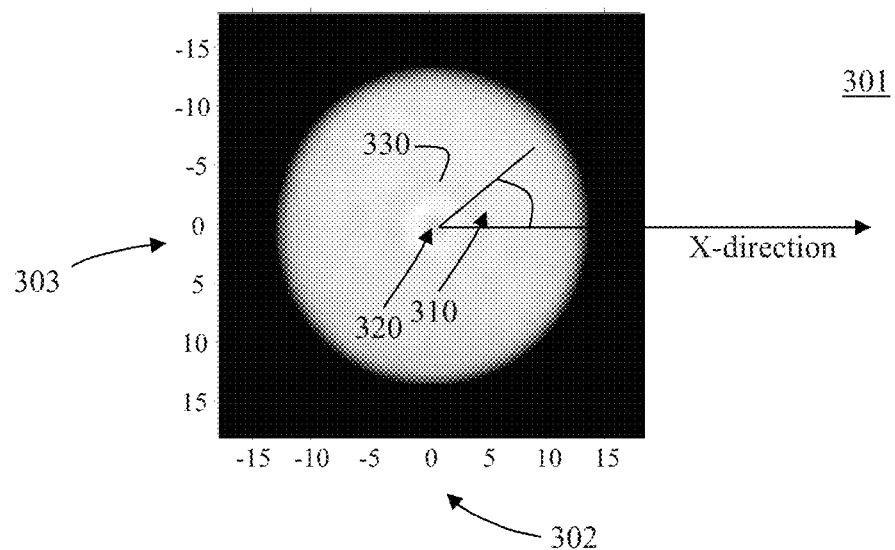
FIG. 3 shows a two-dimensional transverse distribution of spontaneous emission measured in a Yb-doped silica optical fiber, according to an embodiment.

FIG. 3 shows a two-dimensional transverse distribution 303 of spontaneous emission measured for an optical fiber, according to an embodiment. For example, an optical fiber may comprise a Yb-doped silica optical fiber, though claimed subject matter is not limited in this respect. Distribution 303 may be determined using any of a number of techniques, including an inverse Radon transform. In one implementation, spontaneous emission may be measured at a plurality of azimuthal angles 310 about an axial center 320 of an optical fiber. Scale 302 may indicate a distance in microns from center 320 along an X-direction and scale 303 may indicate a distance from center 320 in microns substantially perpendicular to the X-direction. In the particular example shown in FIG. 3, distribution 303 may be determined using an inverse Radon transform based, at least in part, on thirty-six spontaneous emission measurements for an optical fiber at azimuthal angles 310 comprising 0, 5, 10, . . . 175 degrees, respectively. Features included in a two-dimensional radial distribution, such as 303, may indicate various aspects of a measured optical fiber. For example, among a number of other features, a ring-like structure 330 may comprise a vestige from a fiber manufacturing process. For example, a ring-like structure may be obtained from a collapse of a hollow tube whose inner walls were previously impregnated with dopant species.

Figure 4:
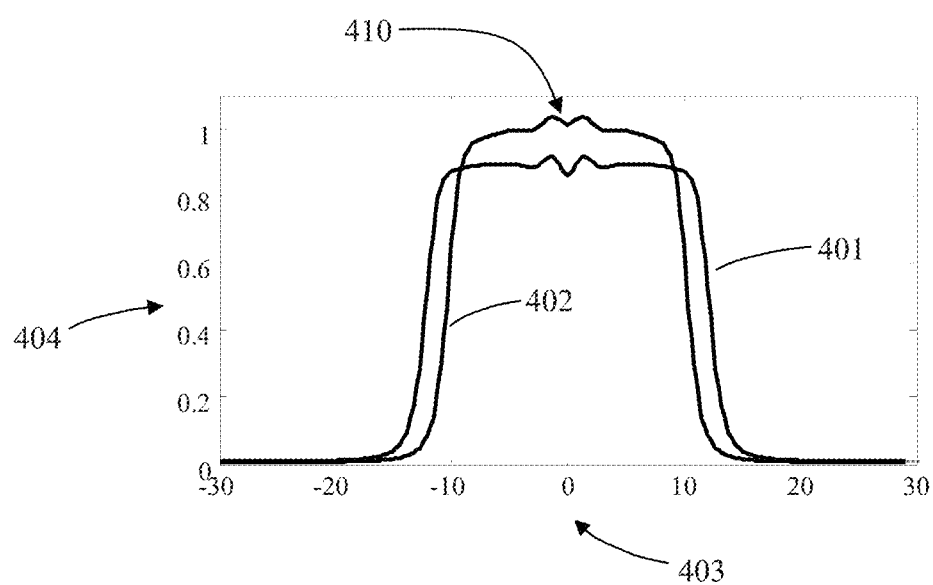
FIG. 4 compares transverse spontaneous emission profiles measured for two different Yb-doped silica optical fibers, according to an embodiment.

FIG. 4 compares transverse spontaneous emission profiles measured for two Yb-doped silica optical fibers, according to an embodiment. For example, spontaneous emission profile 401 for one optical fiber and spontaneous emission profile 402 for another optical fiber may be determined using an inverse Radon transform. For a particular example, one optical fiber may comprise a 25-micron diameter Yb-doped fiber and the other optical fiber may comprise a 20-micron diameter Yb-doped fiber. Scale 403 may indicate a distance in microns from a center of a measured optical fiber substantially along a radial direction and scale 404 may indicate relative magnitude in arbitrary units. A difference of the two optical fibers in core size or relative spontaneous emission may be apparent by comparing profiles 401 and 402. For example, both fibers show a fine ripple structure 410 that may comprise a vestige from a fiber manufacturing process. As indicated, a fine ripple structure may be associated with a collapse of a hollow tube whose inner walls were previously impregnated with dopant species, for example. Relative amplitude of spontaneous emission may be higher in the core region of profile 410 relative to the core region of profile 401, which may indicate that gain efficiency is higher in one core region compared to the other, for example.

In an embodiment, a system, such as 100 described above, may be used to probe an optical fiber having a distribution of gain-producing dopants that is not uniform along a length of the optical fiber. For example, an optical fiber that is tapered along its length may comprise a non-uniform distribution of gain-producing dopants. For another example, an optical fiber assembly that includes a fusion splice between two or more optical fibers may comprise a non-uniform distribution of gain-producing dopants. For non-uniform distribution of gain-producing dopants in an optical fiber, measurements may be performed at a number of discrete axial positions by translating the optical fiber in discrete operations through a measurement zone, for example. Alternatively, if a two-dimensional array detector is arranged so that a particular axis of the array substantially corresponds to an axial direction of an optical fiber, a varying distribution of optical gain measured at different axial positions may be observed along the particular axis, for example.

While examples involve active optical fibers intended for producing optical gain, embodiments may involve a spatial distribution of non-gain producing dopants in a passive optical fiber. For example, a germanium oxide dopant used in passive silica optical fibers may be excited by UV radiation and may spontaneously emit in a visible band. Accordingly, passive telecommunications fibers doped with germanium oxide, among a number of other types of optical fibers, may be probed by pumping with UV radiation. In this way, a spatial distribution of germanium oxide dopant species may be determined.

It is understood that while examples described here may apply to rare-earth dopants in fused silica optical fibers, embodiments may also be applied to non-silica optical fibers such as chalcogenide, fluoride, phosphate, YAG, or polymer optical fibers. A pumping signal wavelength may be selected to correspond to an absorption wavelength of a dopant species in a host material of an optical fiber to be measured. Also, refractive index fluid may be selected to correspond to a refractive index of a host material of an optical fiber to be measured.

In another embodiment, a system, such as 100, may be used to measure any of a number of spectral characteristics of a fluid inside a capillary tube. For example, a capillary tube containing a flowing or stationary fluid may be measured in a similar fashion to that described by optical fiber 114, though claimed subject matter is not so limited.

In yet another embodiment, a system, such as 100, may be used to measure any of a number of spectral characteristics, such as a spatial distribution or optical gain efficiency of gain-producing dopants in an optical fiber while the optical fiber transmits an optical signal, for example.

It will, of course, be understood that, although particular embodiments have just been described, claimed subject matter is not limited in scope to a particular embodiment or implementation. For example, one embodiment may be in hardware, such as implemented on a device or combination of devices, for example. Likewise, although claimed subject matter is not limited in scope in this respect, one embodiment may comprise one or more articles, such as a storage medium or storage media that may have stored thereon instructions capable of being executed by a specific or special purpose system or apparatus, for example, to result in performance of an embodiment of a method in accordance with claimed subject matter, such as one of the embodiments previously described, for example. However, claimed subject matter is, of course, not limited to one of the embodiments described necessarily. Furthermore, a specific or special purpose computing platform may include one or more processing units or processors, one or more input/output devices, such as a display, a keyboard or a mouse, or one or more memories, such as static random access memory, dynamic random access memory, flash memory, or a hard drive, although, again, claimed subject matter is not limited in scope to this example.

In the preceding description, various aspects of claimed subject matter have been described. For purposes of explanation, specific numbers, systems, or configurations may have been set forth to provide a thorough understanding of claimed subject matter. However, it should be apparent to one skilled in the art having the benefit of this disclosure that claimed subject matter may be practiced without those specific details. In other instances, features that would be understood by one of ordinary skill were omitted or simplified so as not to obscure claimed subject matter. While certain features have been illustrated or described herein, many modifications, substitutions, changes, or equivalents may now occur to those skilled in the art. It is, therefore, to be understood that the appended claims are intended to cover all such modifications or changes as fall within the true spirit of claimed subject matter.

What is claimed is:

1. A method comprising:
    exposing an optical fiber to transverse pump irradiation; and
    radially measuring transverse spatial distribution of spontaneous emission produced in said optical fiber in response to said transverse pump irradiation, and wherein said transverse spatial distribution of spontaneous emission is based, at least in part, on a type of gain-producing dopants in said optical fiber and on a distribution of gain-producing dopants in said optical fiber.

2. The method of claim 1, wherein said exposing is performed so as to not result in single-mode or multi-mode optical signal transmission at a wavelength of said transverse pump irradiation sufficient to significantly impact said measuring transverse spatial distribution.

3. The method of claim 1, wherein said transverse pump irradiation comprises substantially homogeneous transverse pump radiation.

4. The method of claim 1, wherein said measuring said transverse spatial distribution of spontaneous emission of said optical fiber further comprises measuring at multiple angles of rotation; and
wherein the method further comprises processing said measured transverse spatial distribution of spontaneous emission measured at said multiple angles of rotation using tomography.

5. The method of claim 1, wherein said optical fiber comprises a capillary tube containing a flowing or stationary fluid.

6. The method of claim 1, further comprising transmitting axially an optical signal in said optical fiber during said measuring.

7. The method of claim 1, wherein said optical fiber comprises a silica glass fiber doped with one or more rare-earth materials.

8. The method of claim 1, further comprising coupling said transverse pump irradiation to said optical fiber using a refractive index fluid.

9. The method of claim 1, wherein said measuring transverse spatial distribution of spontaneous emission further comprises imaging said spontaneous emission using an oil-immersion objective lens.

10. The method of claim 1, further comprising attenuating selected frequencies of said transverse pump irradiation using an optical filter while not substantially attenuating said spontaneous emission.

11. A system for radially measuring transverse spatial distribution of spontaneous emission produced in an optical fiber, the system comprising:
a pump radiation source to transversely irradiate said optical fiber with radiation to produce said spontaneous emission; and
an objective lens, a multi-pixel detector, and a processor;
wherein said objective lens, said multi-pixel detector, and said processor in combination to radially measure said transverse spatial distribution of spontaneous emission, and wherein said transverse spatial distribution of spontaneous emission is to indicate, at least in part, a type or location of said gain-producing dopants in said optical fiber.

12. The system of claim 11, wherein said radiation comprises substantially homogeneous transverse pump radiation.

13. The system of claim 11, further comprising:
a rotation stage to rotate said optical fiber to any of a plurality of rotation angles relative to said objective lens.

14. The system of claim 11, wherein said optical fiber comprises a silica glass fiber doped with one or more rare-earth materials.

15. The system of claim 11, wherein said pump radiation source further comprises a pump fiber, and wherein an end face of said pump fiber and said optical fiber are optically coupled via a refractive index fluid.

16. The system of claim 11, wherein said objective lens comprises an oil-immersion objective lens.

17. The system of claim 11, further comprising a filter to attenuate selected frequencies of said radiation while not substantially attenuating said spontaneous emission.

18. The system of claim 11, wherein said filter is disposed between said objective lens and said multi-pixel detector.

19. The system of claim 11, wherein said optical fiber comprises a non-axisymmetric optical fiber.

20. A device comprising a non-transitory computer-readable storage medium having executable instructions stored thereon for use with a system comprising a pump radiation source in relation to an optical fiber, the executable instructions to:
expose said optical fiber to transverse pump irradiation; and
radially measure transverse spatial distribution of spontaneous emission produced in said optical fiber in response to said transverse pump irradiation, and wherein said transverse spatial distribution of spontaneous emission is to indicate, at least in part, a type or location of said gain-producing dopants in said optical fiber.

21. The device of claim 20, wherein said instructions to measure said transverse spatial distribution of spontaneous emission of said optical fiber to further measure at multiple angles of rotation; and
wherein said instructions to further process said measured transverse spatial distribution of spontaneous emission measured at said multiple angles of rotation using tomography.

22. The device of claim 20, wherein said system further comprises an optical filter and said instructions are further to attenuate selected frequencies of said transverse pump irradiation using said optical filter and to not substantially attenuate said spontaneous emission.

* * * * *